United States Patent [19]

Hurni et al.

[11] Patent Number: 5,091,300
[45] Date of Patent: Feb. 25, 1992

[54] RADIO-IMMUNO ASSAY FOR HEPATITIS B VIRUS PRES2 ANTIBODIES

[75] Inventors: William M. Hurni; William J. Miller, both of North Wales, Pa.

[73] Assignee: Merck & Co., Inc., Rahway, N.J.

[21] Appl. No.: 389,207

[22] Filed: Aug. 3, 1989

[51] Int. Cl.$^5$ .............................................. C12Q 1/70
[52] U.S. Cl. ................................... 435/5; 435/235.1; 435/810; 435/948; 436/501; 436/518; 436/534; 436/543; 436/547; 436/804; 436/808; 436/820
[58] Field of Search ................ 435/5, 235.1, 948, 810; 436/501, 518, 534, 543, 547, 804, 808, 820

[56] References Cited

U.S. PATENT DOCUMENTS

| | | | |
|---|---|---|---|
| 4,876,191 | 10/1990 | Hollander et al. | 436/518 |
| 4,963,483 | 10/1990 | Ellis et al. | 435/69.3 |
| 5,028,524 | 7/1991 | Fujisawa et al. | 436/534 |

OTHER PUBLICATIONS

Hurni, W. M. et al., J. Med. Virol. (Submitted 1989).
Coursaget, P. et al., Vaccine 6, pp. 357–361 (1988).
Budkowska, A., et al., Journal of Immunological Methods, 102, pp. 85–92 (1987).
Neurath, A. R. et al., Vaccine, 4, pp. 35–37 (1986).
Neurath, A. R. et al., Journal of General Virology, 67, pp. 453–461 (1986).

*Primary Examiner*—Mary E. Ceperley
*Attorney, Agent, or Firm*—Hesna J. Pfeiffer; Raymond M. Speer

[57] ABSTRACT

Anti-hepatitis B virus surface protein (anti-HBS) antibody is adsorbed onto the surface of a substratum. Hepatitis B virus PreS2+S (PreS2+S) protein is then adsorbed onto the same surface through the interaction of the anti-HBS antibody with the "S" portion of the PreS2+S protein. The coated surface is then incubated concomitantly with the test sample and a radiolabelled antibody specific for the "PreS2" portion of the PreS2+S protein.

3 Claims, No Drawings

RADIO-IMMUNO ASSAY FOR HEPATITIS B VIRUS PRES2 ANTIBODIES

BACKGROUND OF THE INVENTION

A recombinant hepatitis B virus vaccine (Recombivax HB) has been available for human use since 1986. This vaccine consists of 20 nanometer particles which are exclusively made up of hepatitis B virus surface protein (HBS) and has been proven to efficiently elicit hepatitis B virus (HBV) neutralizing antibodies. Subsequently it became evident that an additional amino acid sequence, which is an $NH_2$-terminal extension of the HBS protein known as PreS2, was also important in HBV immunity. It was then thought that including PreS2 in a HBV vaccine could have beneficial effects.

A second generation HBV vaccine consisting of recombinant hepatitis B virus PreS2+S antigen (PreS2+S) is currently being developed for use in humans. Antibodies generated against the PreS2 region of the PreS2+S antigen have been shown to block infectivity of HBV. The PreS2 region of the protein has been recently demonstrated to contain immunodominant epitopes for the generation of HBV neutralizing antibodies. The importance of antibodies to the PreS2 region in the course of human disease is underscored by a direct correlation of the presence of anti Pre-S2 antibodies with convalescence from hepatitis B virus (HBV) infection.

Following vaccination with the recombinant PreS2+S antigen the patient's ability to achieve a high titer of anti PreS2 antibodies will, in turn, directly correlate with protection from HBV infection or minimization of disease. It is therefore essential that the antibody response to PreS2 is assayed without interference from anti-S antibodies, despite the fact that PreS2 and S are parts of one continuous peptide.

Currently, assay systems are available for the detection of anti-PreS2 antibodies. Many of these assays incorporate the PreS2 epitope in the form of short synthetic peptides comprising parts or all of PreS2. Small peptides or fragments of larger proteins may not present an appropriate structural conformation for maximal antibody recognition and may therefore misrepresent natural antigen-antibody interaction.

Furthermore, these assay systems employ as the mode of detection, a radiolabelled or enzyme conjugated antibody specific for antibodies of the test sample source, e.g. $^{125}$I-labelled or alkaline phosphatase-conjugated anti-human IgG, for detecting anti-PreS2 antibodies in human serum. This can lead to increased background interference due to: i) non-specific interactions with antibodies in the test sample which are not specific for PreS2; ii) non-specific interactions of the labelled detector antibody with components of the assay apparatus, and; iii) specific interactions of the labelled detector antibody with antibodies from the test sample which are non-specifically adsorbed to the assay apparatus.

OBJECTS OF THE INVENTION

It is the object of the present invention to provide an improved radio-immuno assay for anti-PreS2 antibodies. Another object is to provide an assay which has reduced non-specific background interference. An additional object of this invention is to provide an assay which selectively measures anti-PreS2 antibodies only. These and other objects of this invention will be apparent from the following description.

SUMMARY OF THE INVENTION

This invention provides a method for measuring the amount of anti-PreS2 antibody present in a biological fluid. A biological fluid as referred to herein, can consist of but is not limited to, blood, serum, plasma or any blood product, bodily secretions and excretions, tissues or tissue extracts, and cell culture fluid or cell culture extracts.

Anti-HBS antibody is adsorbed onto the surface of a substratum. A limiting amount of PreS2+S protein is then adsorbed onto this surface by virtue of the interaction of the anti-HBS antibody with the "S" portion of the PreS2+S protein (the adsorption of PreS2+S is conducted in the presence of an agent which can occupy all remaining sites available for non-specific interactions, e.g. BSA). The coated surface is then incubated concomitantly with the test sample and radiolabelled anti-PreS2 antibody. The amount of radiolabel bound to the surface determines the amount of, or the presence or absence of anti-PreS2 antibody in the test sample.

DETAILED DESCRIPTION OF THE INVENTION

The present invention relates to a radio-immuno assay (RIA) for anti-PreS2 antibody.

The starting material for the RIA of this invention is anti-hepatitis B virus surface protein (anti-HBS) antibody. Anti-HBS antibody can be obtained from various sources, including but not limited to, naturally infected or immunized humans and laboratory animals, or from a recombinantly engineered host cell or animal. The anti-HBS antibody can be, but is not limited to, polyclonal or monoclonal antibodies or fragments thereof, and may be in the form of, but not limited to, serum, plasma, ascitic fluid, cell culture fluid, cell extracts or purified from the above. The preferred source is human serum or plasma, from an individual known to have high levels of anti-HBS antibody (AUSAB titer of about $1 \times 10^5$ MIU/ml).

The anti-HBS antibody is used to coat the surface of a suitable substratum. The most common types of substrata are made of plastic, including but not limited to, polyethylene, polypropylene or polystyrene, with polystyrene being the preferred plastic. The substratum can be formed into various shapes, including but not limited to, tubes, dishes, plates, multiwell plates, beads or any vessel, with beads being the most preferred form. The beads can have a wide size range, the most preferred size being about 6.3 mm in diameter.

The anti-HBS coated bead is then incubated with a solution of PreS2+S protein which may be obtained by, but not limited to, synthetic techniques, recombinant DNA techniques or from natural sources. During this incubation step PreS2+S is adsorbed onto the bead via the specific interaction of the "S" portion of the PreS2+S protein with the anti-HBS coating the bead surface. This adsorption procedure results in a limiting amount of PreS2+S protein bound to the bead surface. Included in the PreS2+S protein solution is a material adapted to occupy substantially all of the remaining sites available for non-specific adsorption. Examples of such materials are serum albumin, serum, and milk. The most preferred material for this purpose is bovine serum albumin (BSA) at a concentration of about 1%. To ensure uniform coating of the beads, a large batch of beads is prepared at once and the coating steps are done with constant, gentle tumbling.

Beads (or any other substratum) prepared as described above, may be stored. Following preparation, the substratum is dried, sealed in a suitable container and stored at about −20° C. for varying lengths of time.

A sample of a biological fluid to be tested for the presence of anti-PreS2 antibodies (test sample) is mixed with a known quantity of $^{125}$I-radiolabelled anti-PreS2 antibody (typically about $3 \times 10^5$ cpm) The test sample may be used undiluted or a series of dilutions may be prepared. This mixture is then incubated with the previously described coated bead.

It will be obvious to those skilled in the art that other means of labelling the anti-PreS2 antibody are suitable. The other means of labelling include, but are not limited to, different isotopes (e.g. $^3H$, $^{32}P$, $^{35}S$, $^{14}C$), enzymes (e.g. peroxidase, alkaline phosphatase), and fluorescent moieties (e.g. fluorescein, rhodamine). In addition, it will be obvious to those skilled in the art that polyclonal or monoclonal antibodies as well as fragments of antibodies are suitable for labelling and use in this procedure.

A separate but similar test sample which is known to be free of anti-PreS2 antibodies (negative control) is also mixed with the same amount of radiolabelled anti-PreS2 antibody and incubated with a prepared bead. Additionally, a separate but similar test sample which is known to contain anti-PreS2 antibodies (positive control) is mixed with the same quantity of radiolabelled anti-PreS2 antibody and incubated with a prepared bead. Following incubation with the test samples the beads are extensively washed with PBS, and the amount of bead-bound radioactivity is measured.

This procedure is a "competitive assay" in which anti-PreS2 antibodies present in the test samples compete with the radiolabelled anti-PreS2 antibody for the PreS2 binding sites on the coated bead. Therefore, higher levels of bead bound radioactivity indicate lower levels of anti-PreS2 antibodies in the test samples and, conversely, lower levels of bead bound radioactivity indicate higher levels of anti-PreS2 antibodies in the test samples. It is also important that the amount of PreS2+S coating the bead is limiting because excessive PreS2+S would interfere with the competition for PreS2 epitopes by the radiolabelled antibody and anti-PreS2 in the test sample.

This assay can be used to detect the presence of anti-PreS2 antibodies in patients having naturally occurring HBV infection or following vaccination. It is especially useful for determining the outcome of the vaccination of humans with PreS2 containing vaccines.

The following examples illustrate the present invention without limiting the same thereto.

EXAMPLE 1

Step A: Human serum known to contain a high titer (AUSAB titer of about $1 \times 10^5$ MIU/ml) of anti-HBS antibodies is diluted 1:100 using a buffer solution of sodium carbonate (about 0.08M) pH 9.6 as the diluent. This diluted serum is used to coat polystyrene beads (6.4 mm diameter). The beads are added to the diluted serum until the top of the bead layer is just beneath the surface of the diluted serum. Typically about 150 ml of serum solution is used. The beads are incubated in the serum solution overnight (about 15 hours) at 4° C. to effect coating. The coating solution is then drained and the beads are extensively washed with distilled water (at least 5 times). The beads are then air dried and can be stored in a closed glass bottle at −20° C.

Beads coated with anti-HBS antibodies are then incubated in a solution of PBS containing 1% BSA and 5 ng/ml PreS2+S protein. Typically the beads coated with anti-HBS antibodies are added to 150 ml of the PreS2+S solution until the top of the bead layer is just beneath the surface of the PreS2+S solution. he beads are incubated for about 5 hours at room temperature with gentle rotation. The PreS2+S solution is drained and the beads are extensively washed with distilled water (at least 5 times). The beads are then air dried and can be stored in sealed bottles at −20° C.

Step B: A volume of radiolabelled ($^{125}$I) monoclonal anti-PreS2 antibody containing about $3 \times 10^5$ cpm (usually 10 ul) is placed in each well of a plastic multiwell plate (usually a 20 well plate). 0.2 ml of serum from a patient vaccinated with PreS2+S (unknown test sample) is added to individual wells. Ten wells receive 0.2 ml of negative control sample containing no anti-PreS2 antibodies and at least two wells receive 0.2 ml of positive control sample known to contain anti-PreS2 antibodies. The samples are thoroughly mixed and one PreS2+S protein-coated bead is added to each well containing a test sample or control sample. The plate is sealed and incubated for 18–24 hours at room temperature. The beads are each washed three times with 5 ml of distilled water and are individually transferred to plastic tubes for measuring radioactivity (cpm) in a suitable gamma counter. The following results are obtained:

| unknown test sample (dilution) | $^{125}$cpm Obtained | | |
|---|---|---|---|
| | positive control | negative control | cut-off* |
| 1961 (neat) | 709 | 7323 | 4016 |
| 2898 (1:2) | | | |
| 3533 (1:4) | | | |
| 7122 (1:8)[1] | | | |

*The cut-off point is defined as the mean cpm of the negative controls plus the mean cpm of the positive controls, divided by two. An unknown test sample is considered positive for anti-PreS2 antibodies if the cpm is lower than the cut-off.
[1]This dilution failed to meet cut-off criterion and is therefore considered negative for anti-PreS2 antibodies.

EXAMPLE 2

A group of four chimpanzees is immunized with a synthetic peptide corresponding to the PreS2 region of PreS2+S protein. Serum samples are collected from the immunized chimps as well as from two unimmunized chimps. The serum samples are animals have detectable levels of anti-PreS2 antibodies whereas the two unimmunized animals have no detectable anti-PreS2 antibodies.

EXAMPLE 3

The procedure of Example 2 except that the chimpanzees were immunized with recombinant, yeast produced PreS2+S protein. Serum from the immunized chimps has detectable levels of anti-PreS2 antibodies.

EXAMPLE 4

A group of normal human volunteers is immunized with recombinant yeast produced PreS2+S protein. Serum samples are collected and an assay for anti-PreS2 antibodies is done according to Example 1, step B. The serum samples are found to contain detectable levels of anti-PreS2 antibodies.

EXAMPLE 5

A group normal human volunteers is vaccinated with recombinant yeast produced PreS2+S protein at varying dosages. Serum samples are collected from the vaccinees at monthly intervals and assayed for the presence of anti-PreS2 antibodies according to Example 1 step B. Individual antibody response curves are generated from the vaccinees over time indicating a successful immunization.

What is claimed is:

1. A method for the detection of anti-PreS2 antibodies in a biological fluid which comprises:
    i) coating the surface of polystyrene beads with anti-HBS antibodies;
    ii) adsorbing PreS2+S protein to the beads via interaction with anti-HBS antibody;
    iii) separately preparing test samples, positive control and negative control samples by mixing each with about $3 \times 10^5$ cpm of $^{125}$I-labelled anti-PreS2 antibody;
    iv) incubating the coated beads from (ii) with the samples prepared in (iii);
    v) measuring the amount labelled anti-PreS2 antibody bound to said beads and calculating the level of anti-PreS2 antibodies in the sample.

2. A polystyrene bead coated with anti-HBS antibody and PreS2+S protein adsorbed to the anti-HBS antibody.

3. A package or kit containing the polystyrene beads of claim 2 which can be used for the detection of anti-PreS2 antibodies.

* * * * *